United States Patent
Frey

(10) Patent No.: US 6,190,375 B1
(45) Date of Patent: Feb. 20, 2001

(54) CORNEAL TISSUE ABLATION DESIGNED FOR DARK ADAPTABILITY

(75) Inventor: Rudolph W. Frey, Orlando, FL (US)

(73) Assignee: Autonomous Technologies Corporation, Orlando, FL (US)

( * ) Notice: Under 35 U.S.C. 154(b), the term of this patent shall be extended for 0 days.

(21) Appl. No.: 09/470,232

(22) Filed: Dec. 22, 1999

Related U.S. Application Data

(63) Continuation of application No. 08/870,168, filed on Jun. 6, 1997, now Pat. No. 6,027,494.

(51) Int. Cl.⁷ .................................................. A61N 5/02
(52) U.S. Cl. .................................................................. 606/5
(58) Field of Search ........................... 606/2–5, 11–14

(56) References Cited

U.S. PATENT DOCUMENTS

| | | | |
|---|---|---|---|
| 5,163,934 | * 11/1992 | Munnerlyn | 606/5 |
| 5,196,027 | * 3/1993 | Thompson et al. | 606/5 |
| 6,027,494 | * 2/2000 | Frey | 606/5 |

\* cited by examiner

*Primary Examiner*—Michael Buiz
*Assistant Examiner*—William Lewis
(74) *Attorney, Agent, or Firm*—Allen, Dyer, Doppelt, Milbrath & Gilchrist, P.A.

(57) ABSTRACT

A system and method for performing a reshaping of a cornea of an eye for improved vision is presented. The system comprises a first appartus for determining dark adapted pupil size of an eye and a second apparatus for reshaping a cornea of the eye in an area approximately equal to the dark adapted pupil size as determined by the first apparatus. The method of the present invention involves dilating the pupil of an eye to its dark adapted size, determining the diameter of the dilated pupil, and ablating the cornea of the eye to match the dilated pupil size. The advantage to using such a system and method when reshaping a cornea of an eye is reduced halo effect or improved night vision.

19 Claims, 2 Drawing Sheets

CORNEAL TISSUE ABLATION DESIGNED FOR DARK ADAPTABILITY

CROSS REFERENCE TO RELATED APPLICATION

This application is a continuation of application Ser. No. 08/870,168, filed Jun. 6, 1997, now U.S. Pat. No. 6,027,494 both of which are commonly owned and assigned with the present invention.

FIELD OF INVENTION

The invention relates generally to a laser system for corneal sculpting. More specifically, it relates to a system and method for determining the dark adapted pupil size of a patient and reshaping the cornea of the eye based on the dark adapted pupil size.

BACKGROUND OF THE INVENTION

Of the various components in the human eye, the cornea is the principal optical element for refracting incident light onto the retina in the form of a clear image. Photorefractive keratectomy (PRK) is a procedure which typically utilizes an excimer laser beam to vaporize "ablate" corneal tissue in a precise manner to correct for focussing deficiencies of the eye. An excimer laser is preferred for this procedure because pulsed ultraviolet ablation is predictable, discrete, and non-damaging to adjacent tissue. PRK generally involves mechanical removal of the epithelium or outer layer of the cornea to expose the Bowman's layer on the anterior surface of the stroma. Laser ablation usually begins at the Bowman's layer. The laser beam removes corneal tissue to varying depths as necessary for recontouring the anterior stroma. Afterward, the epithelium rapidly regrows and resurfaces the contoured area, resulting in an optically correct (or much more nearly so) cornea. In a variation of the procedure, a surface flap of the cornea is folded aside and the exposed surface of the cornea's stroma is ablated to the desired surface shape with the surface flap then being replaced.

The specific region of the cornea involved in the refractive image formation will vary with the size of the pupil. Only a small central corneal region will refract light onto the cornea when the pupil is constricted under bright lighting conditions. Under dim lighting conditions, when the pupil is substantially dilated, a much larger corneal region is involved forming an image on the retina. This variation in pupil size can become an issue for a PRK patient if the diameter of the laser-treated corneal region ("the optical zone") is smaller than the dilated pupil diameter. When the ablated optical zone is smaller than the patient's dark adapted pupil size, the patient's night vision is affected. Typically, the patient's vision will be hazy or somewhat blurred, and the patient may perceive halos around bright lights. Approximately 20 percent of patients treated with a 5 mm optical zone have complained of such problems. This is a result of the pupil becoming larger than 5 mm as the pupil adapts for darkness. When a 6 mm optical zone is ablated, it is estimated that only 2 percent of patients complain of night-vision problems.

One apparent strategy for avoiding such night-vision problems would be to treat all patients with an optical zone larger, much larger, than the maximum pupil diameter. However, there are several disadvantages to this approach. First, maximum pupil diameter varies from patient to patient. Second, the maximum depth of laser ablation and the total volume of tissue removed both increase with optical zone diameter. Such increases typically lead to more regression, that is, deterioration, of the refractive change as the cornea heals. In addition, the increased tissue volume to be removed necessitates a longer laser procedure. Variations in corneal ablation behavior over time due to hydration changes in the de-epithelialized tissue (known to occur) maybe degrade the accuracy of the ablative corneal reshaping for lengthy procedures. A much more desirable strategy, not advanced until the present invention, is to tailor the optical zone diameter in each treatment to the maximum pupil diameter of that patient.

SUMMARY OF THE INVENTION

Accordingly, it is an object of the present invention to provide a system and method for determining the dark adapted pupil size of an eye.

Another object of the present invention is to provide a system and method for determining the dark adapted pupil size of an eye as a tool in ophthalmic laser surgery to include corneal sculpting procedures.

Yet another object of the present invention is to provide a system and method for determining the dark adapted pupil size of an eye that is surgically eye safe.

Other objects and advantages of the present invention will become more obvious hereinafter in the specification and drawings.

In accordance with the present invention, a system and method are provided for performing a reshaping of a cornea of an eye for improved vision. The system comprises a first apparatus for determining dark adapted pupil size of an eye; and a second apparatus for reshaping the cornea of the eye in an area approximately equal to the dark adapted pupil size as determined by the first apparatus. The preferable appartus for determining the dark adapted pupil size of an eye permits tracking the eye as ambient lighting is dimmed down to complete or near-complete darkness with an electrical control of a zoom mechanism. The zoom refers to adjusting the diameter of the spot pattern projected onto the eye. Feed back can be utilized to sense the return from the spots, and then to adjust the zoom so that the spot pattern diameter matches the pupil diameter. Laser ablation would then proceed over that circular region (maybe, plus a little outside). Alternatively, a video system with a circular cursor could be used in dim illumination to identify the position and diameter of the dilated pupil. The zoom mechanism has an electrical control for size adjustment of a beam optical radiation or a plurality of such radiation beams (either at a visible or infra-red wavelength) incident on a boundary coincident with the dark adapted pupil size of the eye. The first apparatus may also comprise delivery optics for focusing a plurality of optical radiation beams on a corresponding plurality of positions located on a boundary coincident with the pupil size of the eye to form a pattern. Zoom optics may be used for adjusting the pattern formed by the plurality of optical radiation beams incident on said corresponding plurality of positions. An optical receiving arrangement for detecting reflected energy from each of the plurality of positions is also employed to determine the dark adapted pupil size. The pattern formed by the plurality of optical radiation beams is equivalent to the dark adapted pupil size of the eye. The dark adapted pupil size is entered into a computer program for corneal sculpting.

In performing laser reshaping of an eye for improved vision, the diameter of the optical zone ablated on the cornea is adjusted to match, or nearly match, the diameter of the dilated pupil. The ablation profile at the periphery of the optical zone may be tapered to form a smooth transition between treated and untreated portions of the eye.

This patent application is copending with related PCT patent applications entitled, "Laser Sculpting Method and System", International publication number WO 95/28890; "Eye Movement Sensing Method and System", International publication number WO 95/28879; and "Laser Beam Delivery and Eye Tracking System", International publication number WO 95/28989 all of which were published on Nov. 2, 1995, and owned by a common assignee of subject PCT applications. The disclosures of these three applications all of which are based on United States patent applications, are incorporated herein by reference.

DETAILED DESCRIPTION OF THE INVENTION

Figure 1A:
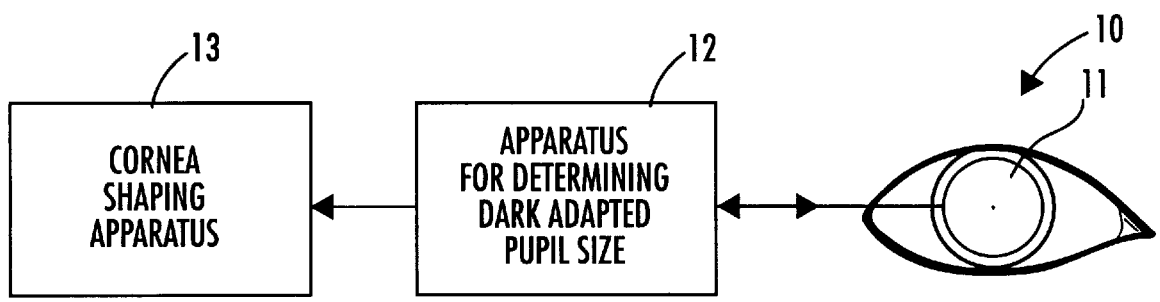
FIG. 1A is a block diagram of the system of the present invention.

Referring now to the drawings, and more particularly to FIG. 1A, a block diagram of the system of the present invention is shown. The eye 10 is shown with an enlarged pupil 11 which has been adapted to its dark adapted size. As the lights are dimmed or the pupil is otherwise enlarged to a dark adapted pupil size such as by dilation by appropriate eye drops, the apparatus for determining dark adapted pupil size 12 emits at least one invisible beam of light onto the eye to form one or more spots for defining the size of the dark adapted pupil. The size of the spot is adjusted to match the size of the dark adapted pupil 12 by focussing on the pupil/iris boundary. The measured diameter of the spot size is then input into a program which is used to run the cornea shaping apparatus 13. The zone which is ablated under the corneal sculpting program is just a little larger in diameter than the dark diameter of the adapted pupil to allow for a smooth transition between the treated and untreated portion of the eye.

Figure 1B:
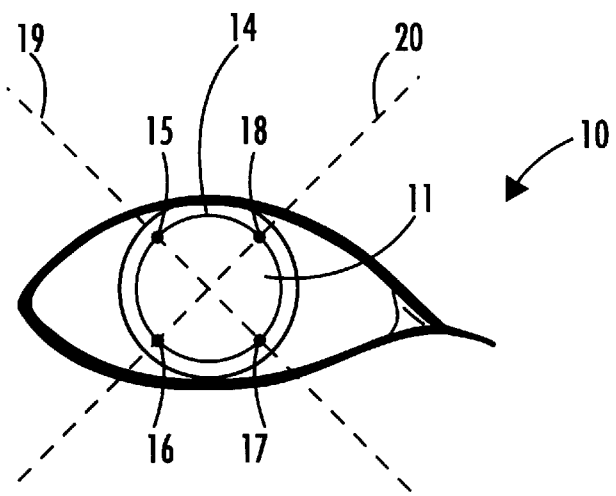
FIG. 1B is a plan view of an eye showing four light spots positioned on the eye's iris/dark adapted pupil boundary.

FIG. 1B shows a preferred method for determining the diameter of the dark adapted pupil size 11 of an eye 10. In this method, four spots of light 15, 16, 17 and 18 are positioned on the boundary between the pupil 11 and the iris 14. As the lights are dimmed in the room, the spots of light are used to track the pupil as it dilates. Any movement of the eye may also be tracked using the four spots of light as has been previously disclosed. The wavelength and power of the light spots can be outside the visible spectrum so as not to negate the dark adaptable pupil size or to interfere or obstruct the surgeon's view of the eye undergoing the surgical procedure or injure the subject eye.

Figure 2:
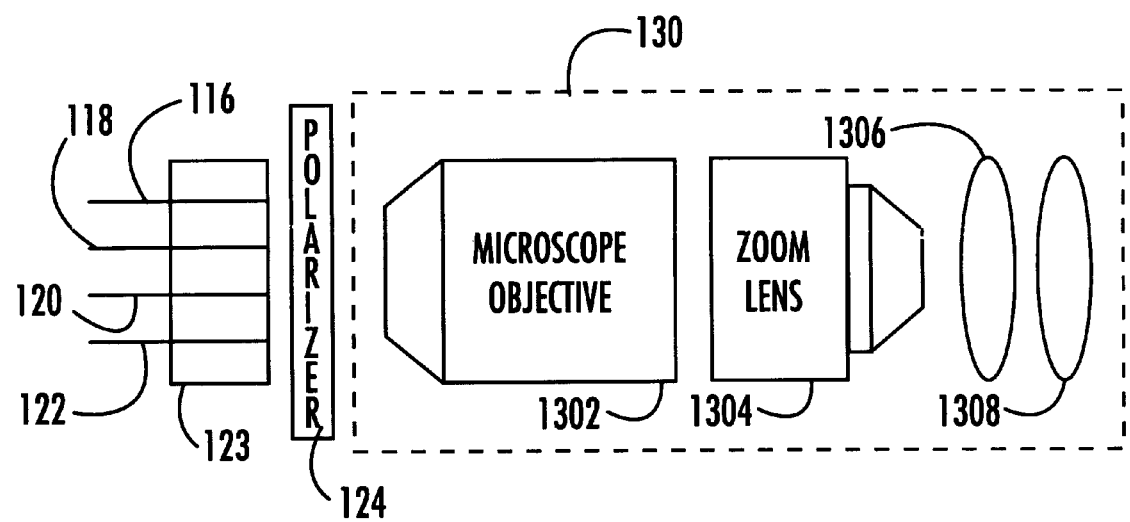
FIG. 2 is a block diagram of a preferred embodiment optical arrangement for the focusing optics of the first appartus.

As a preferred embodiment, the apparatus for determining the dark adapted pupil size and the cornea shaping apparatus for carrying out the method of the invention are described in detail in the aforementioned copending PCT patent applications. However, for the purpose of the present description, the optical arrangement will be described briefly with the aid of the block diagram of FIG. 2. In FIG. 2, fiber optic bundle 123 is positioned at the working distance of microscope objective 1302. The numerical aperture of microscope objective 1302 is selected to be equal to the numerical aperture of fibers 116, 118, 120 and 122. Microscope objective 1302 magnifies and collimates the incoming light. Zoom lens 1304 provides an additional magnification factor for further tunability and for determining the dark adapted pupil size. The zoom lens increases the spot size as the lights ar turned down to examine the patient. Collimating lens 1306 has a focal length that is equal to its distance from the image of zoom lens 1304 such that its output is collimated. The focal length of imaging lens 1308 is the distance to the eye such that imaging lens 1308 focuses the light as four sharp spots on the corneal surface of the eye at the boundary between the pupil and the iris. An optical receiving arrangement detects reflected energy from each of the light spots which is used to measure the diameter of the dark adapted pupil size. This size measurement is subsequently entered into a program for corneal sculpting.

Once the size of the ablation zone is determined, the depth of ablation for each diopter of correction can be determined. For example, if the surgical method requires a 5 mm zone, ablation will only have to go down about 10 microns deep for one diopter of correction. For a 6 mm zone, the ablation would go down about 13 to 15 microns deep for each diopter of correction. The treatment is customized for the needs of the individual, but a lower limit set for approximately 5.5 mm as determined from a statistical data base. Alternatively, the low end limit for the ablation diameter may be the measured diameter of the dark adapted pupil size of the individual.

This method allows for customizing the ablation zone of the patient's dark adapted pupil size to eliminate the halo problem. In turn, this procedure may be done for all of the patients on a customized basis without having to ablate a large volume for patients who only need a smaller volume ablated if they have a smaller dark adapted pupil size.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A method for performing a reshaping of an eye for improved vision, the method comprising the steps of:
    placing an eye within an environment useful in measuring vision of the eye;
    reducing available light within the environment for providing a dark environment within which the eye operates;
    allowing the pupil of an eye to dilated to a size adapted for vision of the eye in the dark environment;
    determining a shape of the dilated pupil; and
    ablating corneal material of the eye over a corneal surface sized approximately to the shape of the dilated pupil.

2. A method according to claim 1, wherein the corneal material ablating step comprises the step of ablating corneal material of the eye to within an ablating diameter approximately sized to within a diameter of the dilated pupil.

3. A method according to claim 2, further comprising the step of inputting the diameter of the dilated pupil into a corneal sculpting program.

4. A method according to claim 1, wherein the dilated pupil shape determining step comprises the steps of placing a light spot on the dilated pupil sufficient for covering the dilated pupil, and measuring a diameter of the light spot.

5. A method according to claim 1, wherein the dilated pupil shape determining step comprises the steps of placing a plurality of light spots onto the eye within the dilated pupil and matching a pattern to the dark adapted size of the pupil, and wherein the corneal ablating step comprises ablating corneal material to proximate the pattern.

6. A method according to claim 1, wherein the cornea material ablating step comprises the step of tapering the cornea to form a smooth transition between treated and untreated portions of the eye.

7. A method for performing a reshaping of an eye for improved vision, the method comprising the steps of:

adding a chemical eye drop onto the eye for dilating the pupil of the eye;

allowing the pupil of the eye to dilate to a size adapted for vision of the eye in a dark environment;

determining a shape of the dilated pupil; and ablating corneal material of the eye over a corneal surface sizes approximately to the shape of the dilated pupil.

8. A method according to claim 7, wherein the corneal material ablating step comprises the step of ablating corneal material of the eye to within an ablating diameter approximately sized to within a diameter of the dilated pupil.

9. A method according to claim 8 further comprising the step of inputting the diameter of the dilated pupil into a corneal sculpting program.

10. A method according to claim 7, wherein the dilated pupil shape determining step comprises the steps of placing a light spot on the dilated pupil sufficient for covering the dilated pupil, and measuring a diameter of the light spot.

11. A method according to claim 7, wherein the dilated pupil shape determining step comprises the steps of placing a plurality of light spots onto the eye within the dilated pupil and matching a pattern to the dark adapted size of the pupil, and wherein the corneal ablating step comprises ablating corneal material to proximate the pattern.

12. A method according to claim 7, wherein the cornea material ablating step comprises the step of tapering the cornea to form a smooth transition between treated and untreated portions of the eye.

13. A method for performing a reshaping of an eye for improved vision, the method comprising the steps of:

dilating the pupil of an eye to a size adapted for vision of the eye in a dark environment;

placing at least one light spot on the dilated pupil sufficient for covering the dilated pupil;

determining a shape of the at least one light spot; and ablating corneal material of the eye over a corneal surface sized approximately to the shape of the at least one light spot.

14. A method according to claim 13, wherein the pupil dilating step comprises the step of reducing available light incident on the eye for providing a dark environment within which the eye operates.

15. A method according to claim 13, wherein the pupil dilating step comprises the steps of adding a chemical eye drop onto the eye for dilating the pupil of the eye, and allowing the pupil of the eye to dilate to the size adapted for vision of the eye in the dark environment.

16. A method according to claim 13, wherein the corneal material ablating step comprises the step of ablating corneal material of the eye to within an ablating diameter approximately sized to within a diameter of the dilated pupil.

17. A method according to claim 16, further comprising the step of inputting the diameter of the dilated pupil into a corneal sculpting program.

18. A method according to claim 13, wherein the at least one light spot comprises a plurality of light spots directed to the dilated pupil, and wherein the shape determining step comprises matching a pattern to the dark adapted size of the pupil.

19. A method according to claim 13, wherein the cornea material ablating step comprises the step of tapering the cornea to form a smooth transition between treated and untreated portions of the eye.

* * * * *